US008409117B2

(12) United States Patent  (10) Patent No.: US 8,409,117 B2
Cheng et al.  (45) Date of Patent: Apr. 2, 2013

(54) WEARABLE DEVICE TO ASSIST WITH THE MOVEMENT OF LIMBS

(75) Inventors: Ching-Hsiang Cheng, Hong Kong (HK); Po Fat Chong, Hong Kong (HK); King Sau Wong, Hong Kong (HK)

(73) Assignee: The Hong Kong Polytechnic University, Kowloon (HK)

( * ) Notice: Subject to any disclaimer, the term of this patent is extended or adjusted under 35 U.S.C. 154(b) by 807 days.

(21) Appl. No.: 12/210,720

(22) Filed: Sep. 15, 2008

(65) Prior Publication Data

US 2010/0069798 A1 Mar. 18, 2010

(51) Int. Cl.
A61H 1/02 (2006.01)
A61H 1/00 (2006.01)

(52) U.S. Cl. ............................................................ 601/5

(58) Field of Classification Search .............. 601/5, 84, 601/97, 98, 101, 104
See application file for complete search history.

(56) References Cited

U.S. PATENT DOCUMENTS

| | | | |
|---|---|---|---|
| 3,683,897 A * | 8/1972 | Shield et al. ................ 601/34 |
| 3,967,321 A | 7/1976 | Ryan et al. | |
| 4,084,267 A | 4/1978 | Zadina | |
| 5,020,790 A | 6/1991 | Beard et al. | |
| 5,103,807 A | 4/1992 | Makaran | |
| 5,112,296 A | 5/1992 | Beard et al. | |
| 5,228,432 A | 7/1993 | Kaiser et al. | |
| 5,231,998 A | 8/1993 | Rosen et al. | |
| 5,285,773 A | 2/1994 | Bonutti et al. | |
| 5,337,737 A * | 8/1994 | Rubin et al. ................ 601/33 |
| 5,456,268 A | 10/1995 | Bonutti | |
| 5,800,561 A | 9/1998 | Rodriguez | |
| 6,379,393 B1 | 4/2002 | Mavroidis et al. | |
| 6,689,074 B2 | 2/2004 | Seto et al. | |
| 6,689,075 B2 | 2/2004 | West | |
| 6,821,259 B2 | 11/2004 | Rahman et al. | |
| 6,827,579 B2 | 12/2004 | Burdea et al. | |
| 7,112,179 B2 | 9/2006 | Bonutti et al. | |
| 7,182,738 B2 * | 2/2007 | Bonutti et al. .............. 601/5 |
| 7,204,814 B2 * | 4/2007 | Peles ............................ 601/5 |
| 7,725,175 B2 * | 5/2010 | Koeneman et al. ...... 600/546 |
| 2001/0029343 A1 * | 10/2001 | Seto et al. ................ 600/587 |
| 2004/0106881 A1 | 6/2004 | McBean et al. | |
| 2006/0161220 A1 * | 7/2006 | Kobayashi et al. ....... 607/49 |
| 2007/0010772 A1 * | 1/2007 | Ryan ........................ 602/26 |
| 2007/0135738 A1 * | 6/2007 | Bonutti et al. .............. 601/5 |
| 2007/0191743 A1 | 8/2007 | McBean et al. | |
| 2008/0077057 A1 * | 3/2008 | Peles ........................... 601/5 |
| 2008/0195005 A1 * | 8/2008 | Horst et al. ................ 601/22 |
| 2009/0306548 A1 * | 12/2009 | Bhugra et al. ........... 600/587 |
| 2010/0280425 A1 * | 11/2010 | Kawakami et al. ....... 601/84 |

* cited by examiner

Primary Examiner — Patricia Bianco
Assistant Examiner — Raymond E Harris
(74) Attorney, Agent, or Firm — Kauth, Pomeroy, Peck & Bailey LLP

(57) ABSTRACT

A wearable device (10) to assist with the movement of limbs (50, 51) connected at a joint (52), the device (50) comprising: a linear motion generating unit (20) to generate linear motion, the unit (20) having distal end portions operatively connected to the limbs (50, 51), whereby the linear motion generated by the unit (20) causes the limbs (50, 51) to move and pivot about the joint (52); a force measuring unit (30) to measure a change of force applied to the limbs or linear motion generating unit (20); and a displacement measuring unit (40) to measure the displacement of the linear motion generating unit (20) when linear motion is generated; wherein a predetermined distance of linear motion having a predetermined velocity is generated by the linear motion generating unit (20) to assist with the movement of the limbs (50, 51) based on the change of force measured by the force measuring unit (30) or the displacement measured by the displacement measuring unit (40).

10 Claims, 9 Drawing Sheets

WEARABLE DEVICE TO ASSIST WITH THE MOVEMENT OF LIMBS

TECHNICAL FIELD

The invention concerns a wearable device to assist with the movement of limbs connected at a joint.

BACKGROUND OF THE INVENTION

Some countries are experiencing an ageing population. Consequently, there is a need to encourage the elderly to maintain their health by performing daily exercise activities. However, most of the elderly, do not regularly exercise to maintain their muscle strength. After retirement, they tend to stay at home and perform minimal exercise.

Disabled people who have suffered a stroke require rehabilitation to help them regain the link from their brain to the muscles of their limbs. Also, people with limb deficiencies and people who wish to exercise more should increase their muscle strength, flexibility, and hand-eye coordination.

Accordingly, there is a desire for a device that is worn by a person to assist with the movement of limbs connected at a joint that can be used safely by the elderly and disabled.

SUMMARY OF THE INVENTION

In a first preferred aspect, there is provided a wearable device to assist with the movement of limbs connected at a joint, the device including:
  a linear motion generating unit to generate linear motion, the unit having distal end portions operatively connected to the limbs, whereby the linear motion generated by the unit causes the limbs to move and pivot about the joint;
  a force measuring unit to measure a change of force applied to the limbs or linear motion generating unit; and
  a displacement measuring unit to measure the displacement of the linear motion generating unit when linear motion is generated;
  wherein a predetermined distance of linear motion having a predetermined velocity is generated by the linear motion generating unit to assist with the movement of the limbs based on the force measured by the change of force measuring unit or the displacement measured by the displacement measuring unit.

The linear motion generating unit may be a linear actuator. The force measuring unit may be a load cell.

The displacement measuring unit may be a potentiometer.

The displacement measuring unit may be positioned on a lead screw of the linear actuator.

The device may further comprise a microcontroller unit (MCU) for processing a feedback control loop to control the operation of the linear motion generating unit using a feedback signal transmitted from the force measuring unit and displacement measuring unit.

The force measured by the force measuring unit may be processed by the MCU to determine the level of voltage to be provided to the linear motion generating unit to generate a corresponding distance of linear motion having a corresponding velocity.

The displacement may be measured by the displacement measuring unit and a time value is recorded.

The device may further comprise a training software module to evaluate the performance of a user using the wearable device in a training exercise by comparing the difference between the recorded displacement and time value against a reference displacement and time value.

The amount of force and displacement of the linear motion generated by the linear motion generating unit may be adjustable depending on whether a user is considered beginner, intermediate or advanced in the level of assistance they require.

The device may be positioned on an inner side of the limbs or on a lateral side of a limb.

The device may further comprise a fastening member to secure the device to the limbs.

The device may further comprise a portable control unit operatively connected to the linear motion generating unit, the portable control unit including a battery to supply power to the linear motion generating unit.

In a second aspect, there is provided a method for assisting with the movement of limbs connected at a joint, the method including:
  generating a linear motion using a linear motion generating unit to cause the limbs to move and pivot about the joint;
  measuring a change of force applied to the limbs or linear motion generating unit;
  measuring the displacement of the linear motion generating unit when linear motion is generated; and
  generating a predetermined distance of linear motion having a predetermined velocity by the linear motion generating unit to assist with the movement of the limbs based on the change of force measured or the displacement measured.

In a third aspect, there is provided a system for assisting with the movement of limbs connected at a joint, the system including:
  a linear motion generating unit to generate linear motion, the unit having distal end portions operatively connected to the limbs, whereby the linear motion generated by the unit causes the limbs to move and pivot about the joint;
  a force measuring unit to measure a change of force applied to the limbs or linear motion generating unit;
  a displacement measuring unit to measure the displacement of the linear motion generating unit when linear motion is generated; and
  a portable control unit operatively connected to the linear motion generating unit, the portable control unit including a battery to supply power to the linear motion generating unit and a processor to control the level of assistance generated by the linear motion generating unit;
  wherein a predetermined distance of linear motion having a predetermined velocity is generated by the linear motion generating unit to assist with the movement of the limbs based on the change of force measured by the force measuring unit or the displacement measured by the displacement measuring unit.

BRIEF DESCRIPTION OF THE DRAWINGS

An example of the invention will now be described with reference to the accompanying drawings, in which.

DETAILED DESCRIPTION OF THE DRAWINGS

Figure 1:
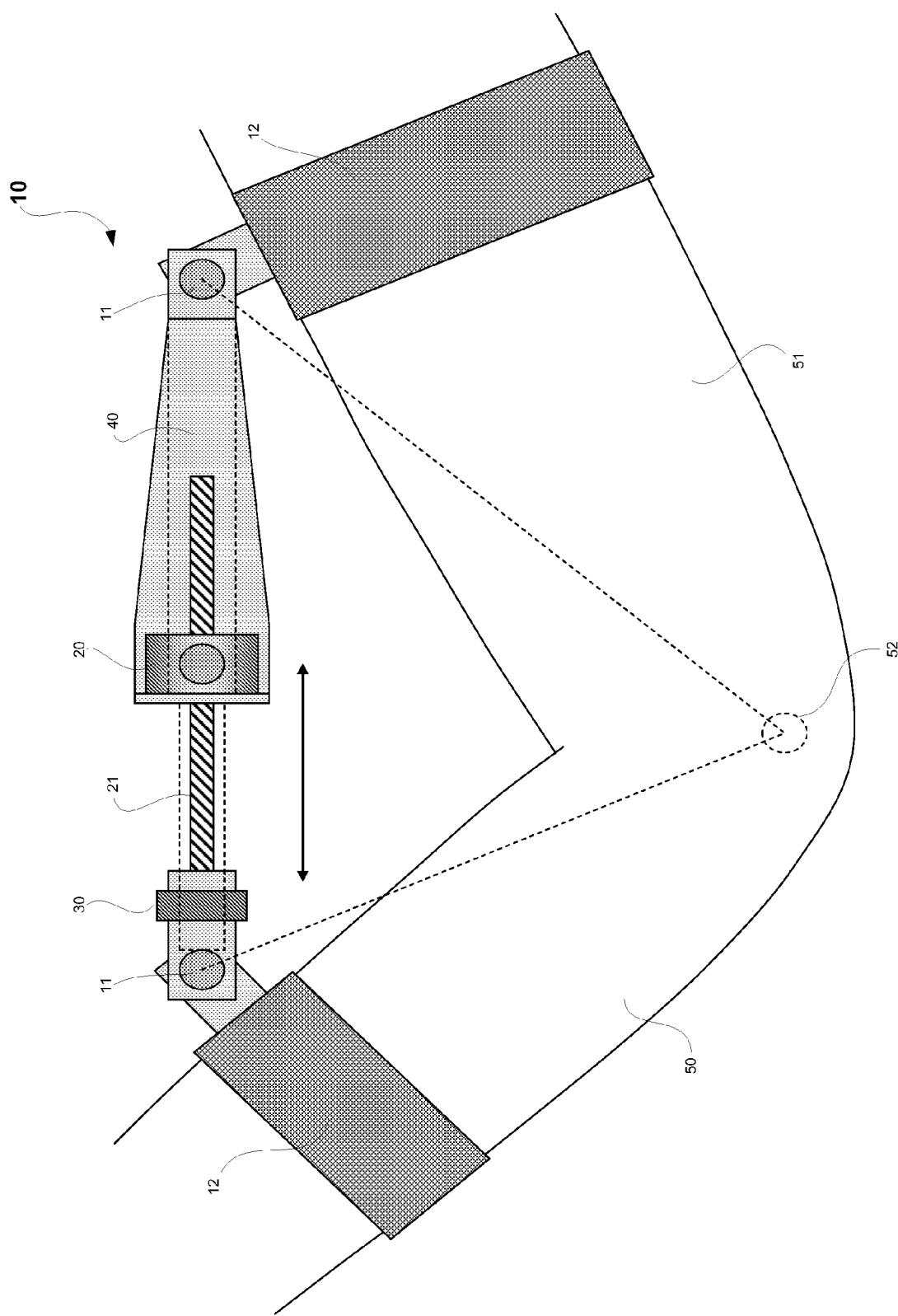
FIG. 1 is a pictorial diagram of a wearable device used for an elbow joint in accordance with an embodiment of the present invention.
Figure 2:
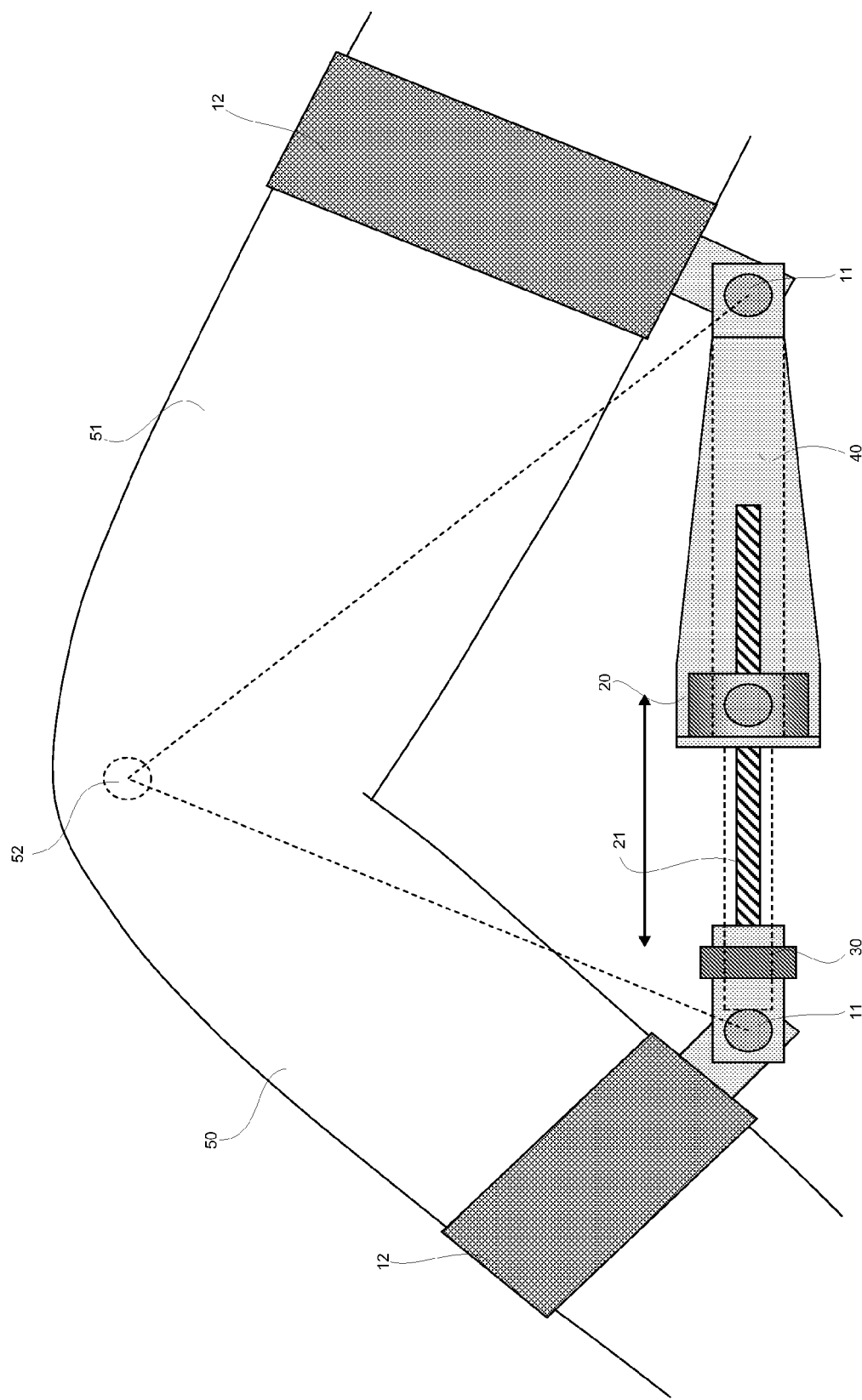
FIG. 2 is a pictorial diagram of a wearable device used for a knee joint in accordance with an embodiment of the present invention.
Figure 3:
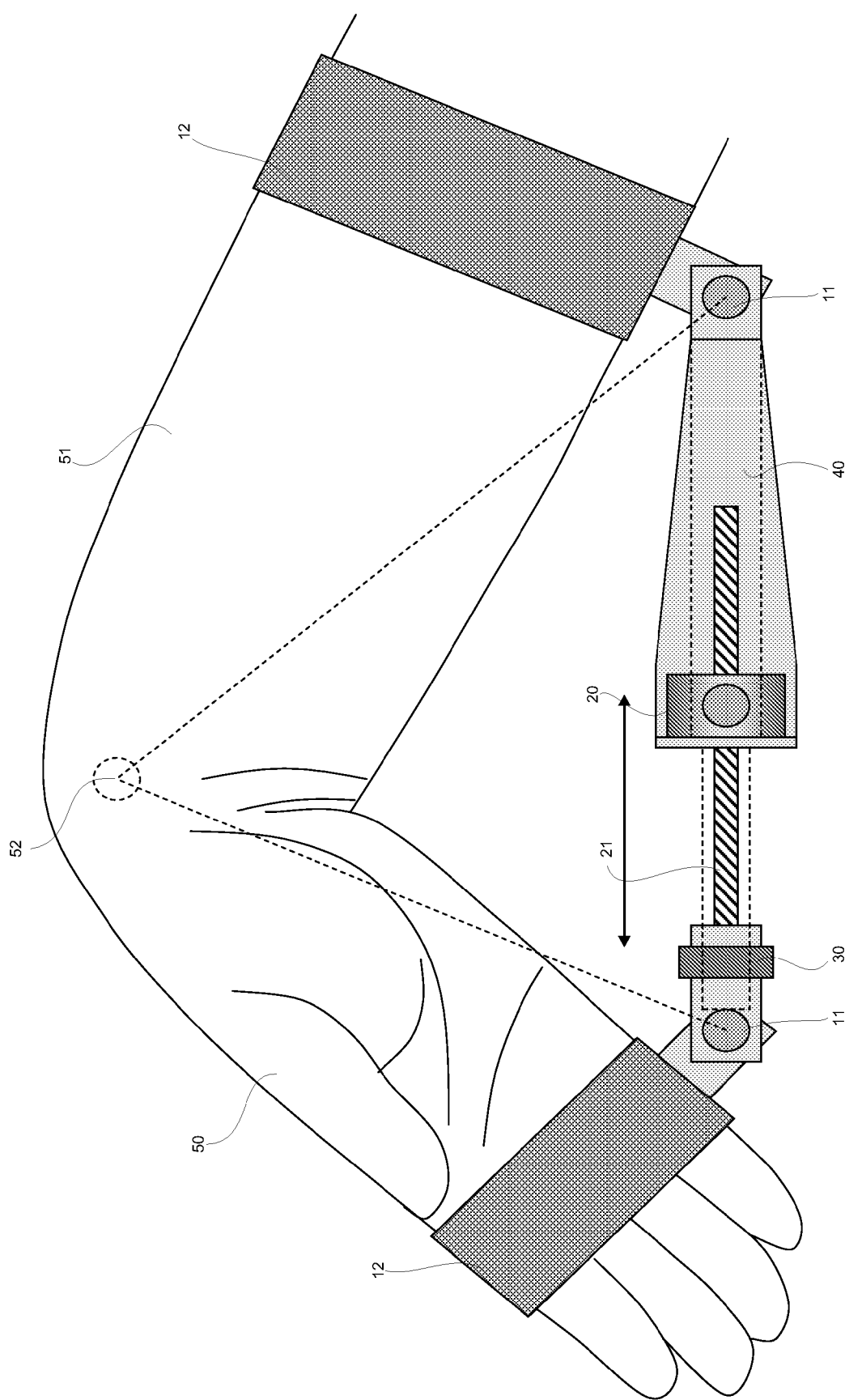
FIG. 3 is a pictorial diagram of a wearable device used for a wrist joint in accordance with an embodiment of the present invention.
Figure 4:
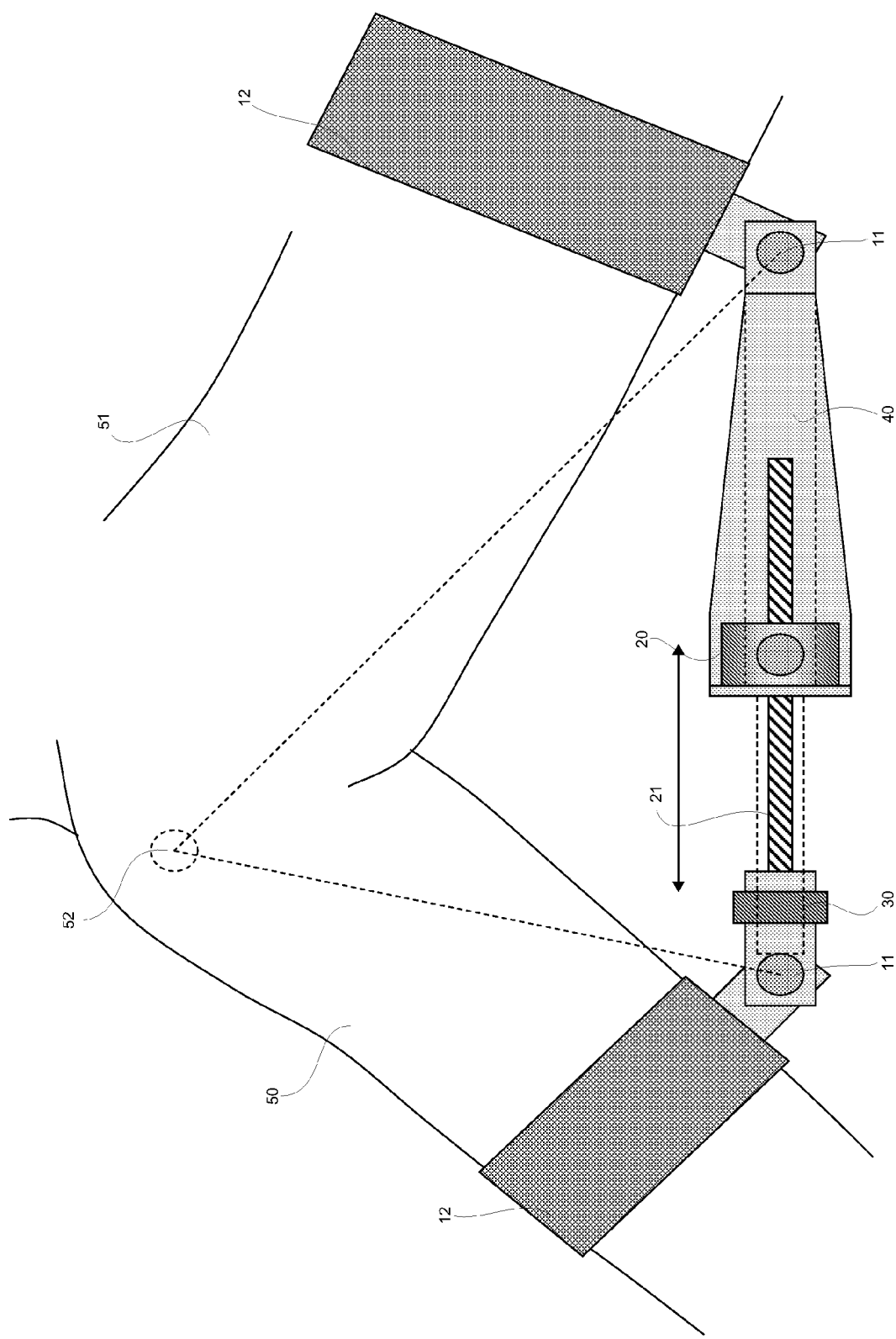
FIG. 4 is a pictorial diagram of a wearable device used for a shoulder joint in accordance with an embodiment of the present invention.

Referring to the drawings, a wearable device 10 to assist the movement of limbs 50, 51 connected at a joint 52 is provided. Generally, the device 10 may be considered a mechanical robotic frame to be worn by the user. The device 10 generally comprises a linear motion generating unit 20, a force measuring unit 30 and a displacement measuring unit 40. The Linear motion generating unit 20 generates linear motion to expand and contract the length of the device 10 along its longitudinal axis. The distal end portions of the device 10 are releasably secured to each respective limb 50, 51. The linear motion generated by the device 10 causes the limbs 50, 51 to move and pivot about the joint 52 thereby assisting with the movement of the limbs 50, 51. The force measuring unit 30 measures a change of force applied to the limbs 50, 51 or linear motion generating unit 20. The displacement measuring unit 40 measures the displacement of the linear motion generating unit 20 when linear motion is generated. A predetermined distance of linear motion having a predetermined velocity is generated by the linear motion generating unit 20. The predetermined distance and predetermined velocity is proportional to the force measured by the force measuring unit 30 or the displacement measured by the displacement measuring unit 40. The amount and speed of the actuation by the linear motion generating unit 20 is based on the force measured by the force measuring unit 30 or the displacement measured by the displacement measuring unit 40.

Preferably, the linear motion generating unit is a linear actuator 20. The linear actuator 20 generates a piston motion in combination with a limb (crank radius) and joint (crank center) to form a kind of crank piston motion. The linear actuator 20 holds the limb 50, 51 at a fixed position without consuming any power. Consequently, this increases battery life usage which means a heavy battery is not required because a great amount of power supply is not required. Using a linear actuator 20 is safer than other actuating devices because if there is a power failure, it can hold the limb 50, 51 at a fixed position. The linear actuator 20 also advantageously provides a large force using only a small stepper motor to accurately deliver incremental movement. This force can be modulated by varying the applied DC voltage. Moreover, the device 10 may rely on this force to exclusively augment voluntary limb movement; for example, the device 10 does not have to employ a pivotal connection at the joint to further constrain limb kinematics. Since the device 10 is a relatively simple mechanism to manufacture, its production cost is reduced which will therefore enhance the market acceptability to elderly people who may not have large financial resources. Advantageously, wearing the device 10 enables indoor exercise training for elderly people. The linear actuator 20 has a motor diameter of 26 mm and the motor may be one that is manufactured by ThomsonAirpax Mechatronics. The linear actuator 20 comprises a stepper motor with a lead screw 21 to convert rotational motion into linear motion. The linear actuator 20 is able to achieve an accuracy of thousandths of an inch (0.001 inch or 0.0254 mm) per step.

Preferably, the force measuring unit is a load cell 30. The load cell 30 measures the force along the lead screw 21 of the linear actuator 20. For example, in the case of lifting an arm 50 to overcome its gravity, the user may not have enough force to lift it. But the change of force (reduction of the tensile force) is measured by the load cell 40 to detect the intention of the user's movement. For example, if the weight of a forearm 50 is 2 kg, the load cell 40 will detect the force to be 1.9 kg, which is higher than a stationary threshold. The linear actuator 20 will be triggered to actuate based on the detected force change (2-1.9) kg=100 g and actuate by a proportional amount. Load cells 30 are generally electronic devices that are used to convert a force into an electrical signal. The load cell 30 is installed on the lead screw 21 of the linear actuator 20 to sense the force applied to the limb. The load cell 30 can also sense the resistance of the limb joint 52. This can prevent injury to the person from over-execution of the actuation force of the linear actuator 20.

The velocity of extending or contracting the linear actuator 20 is determined by the forced measured by the load cell 30. If a force is detected by the load cell 30 that is more than the stationary threshold, a velocity proportional to the detected force is applied until the force is detected to be less than the stationary threshold. The stationary threshold is a force window to allow the linear actuator 20 to be completely stopped even though there may be a small force detected by the load cell 30. The stationary threshold may be user defined. For example, the stationary threshold may be 50 g to 150 g for a person who weighs 50 to 100 kg. The higher the stationary threshold, the higher the initial force change needs to be trigger a movement by the linear actuator 20.

Preferably, the displacement measuring unit is a potentiometer 40. The potentiometer 40 measures the displacement of the piston motion of the linear actuator 20. This enables the detection of the location of the limb joint 51. The potentiometer 40 is placed on the same axis as the linear actuator 20 to closely monitor the displacement of it. The intention of movement of the user's limbs is determined from the input force applied on the load cell 30 or the displacement measured by the potentiometer 40. The level of assistance depends on the input force and displacement of the user.

A microcontroller unit (MCU) 60 is provided for processing a feedback control loop. The feedback control loop controls the operation of the linear motion generating unit using a feedback signal transmitted from the force measuring unit and displacement measuring unit. The force measured by the load cell 30 is processed by the MCU 60 to determine the level of voltage to be provided to the linear actuator. The linear actuator 20 then generates a corresponding distance of linear motion having a corresponding velocity.

A feedback control loop is used to control the linear actuator 20 with a feedback signal from the load cell 30 and potentiometer 40. There are two parameters to be controlled: firstly, the force and secondly, the displacement which corresponds to the voltage and frequency of the linear actuator 20, respectively. Based on the signal level from the load cell 30, the MCU 60 determines what voltage is used on the linear actuator to assist the movement of the limb. The potentiometer provides the actual displacement that has been made from the linear actuator that outputs to the limb to feedback to the MCU 60. It compares the displacement data coded on the excise training program to determine how closely the user has followed the target. The level of the assistance force can be tuned for the user at different training progress.

A training software module 70 is provided to evaluate the performance of a user using the wearable device in a training exercise. The training software module compares the difference between the recorded displacement and time value against a reference displacement and time value. The displacement measured by the potentiometer 40 and a time value is recorded to track the user's performance.

One of many exercise training programs 71 is provided for the training software module 70 to execute. The program 71 is coded with a series of displacement versus time data to be compared with the measured data. In one embodiment, this program 71 is provided in the form of a video game which causes the user to follow a target with their limb, for example, a shooting game. This trains hand-eye coordination to help maintain brain function. The user receives a higher score if they follow the target more closely. The program 71 is designed to have different levels of assistance depending on the progress of the user. It also provides resistance of the user to train their muscle strength after they can overcome the gravitational effect on their limbs. For disabled people, the device 10 may be used for rehabilitating stroke patients to regain the link from their brain to their muscles. The device 10 may be used to assist with the movement of a patient suffering from limb deficiency. For other people, the device 10 may be used as an exercise tool to provide interactive training together with the video game for entertainment. The device 10 may be a multi-purpose platform to be used with different software applications which may provide different training to increase the muscle strength, flexibility, and hand-eye coordination.

The user can be completely passive during a training program 71 so that the linear actuator 20 guides the entire movement of the limbs based on the training program 71. The load cell 30 must continue to monitor for any overload to prevent any injury to the limbs that could be caused by the linear actuator 20 when the limb has a problem with making a movement.

For users at the beginner level, the device 10 can give more assistance by applying more force from the linear actuator 20 and have a better control on the displacement. This can give them more confidence when using the device 10.

For advanced users, the device 10 is able to reduce the level of assistance so that the users move by themselves to follow the target during the training. This includes reducing the force from the linear actuator 20 and lowering the control of the displacement. The user will have a greater chance of missing the target when they do not closely follow the target. When reducing the control of the displacement, sufficient safety for the user must be ensured to prevent any injury to the user caused by additional force or displacement.

The amount of force and displacement of the linear motion generated by the linear actuator 20 is adjustable. The force and displacement is adjusted depending on whether a user is considered a beginner, intermediate or advanced in the level of assistance they require from the linear actuator 20.

Figure 5:
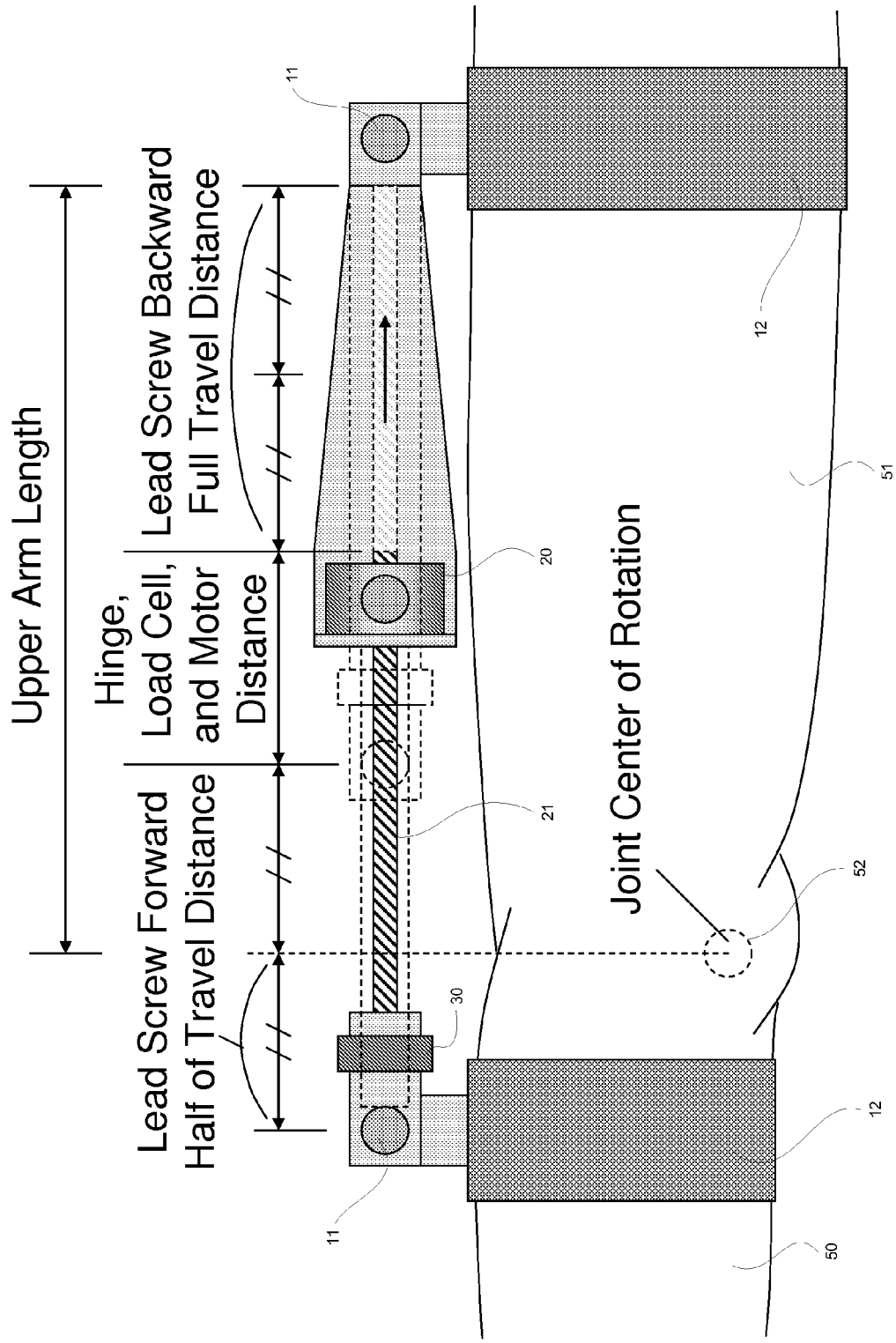
FIG. 5 is a pictorial diagram of a wearable device used for an elbow joint when in an unbent position in accordance with another embodiment of the present invention.
Figure 6:
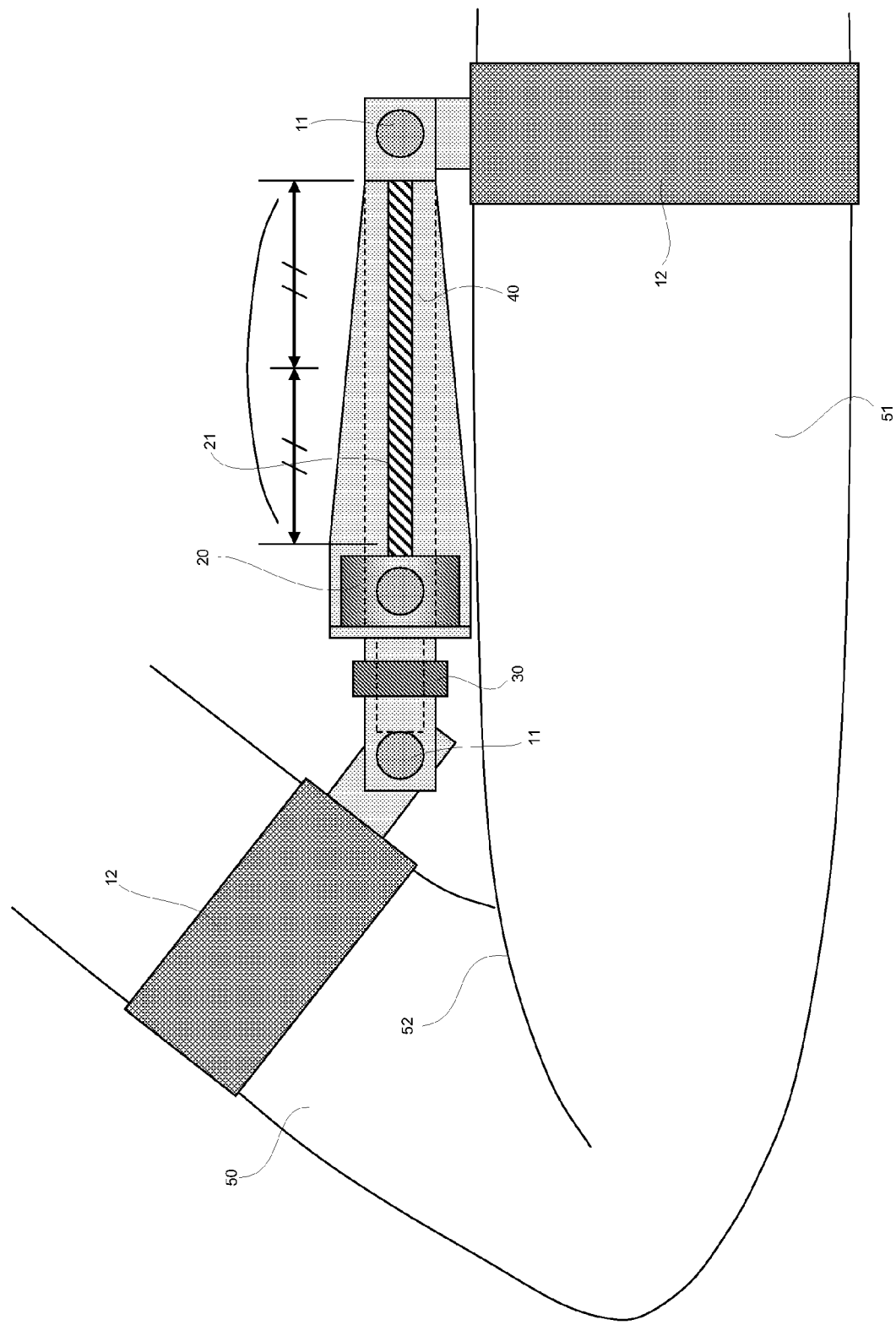
FIG. 6 is a pictorial diagram of a wearable device used for an elbow joint when in a bent position in accordance with another embodiment of the present invention.
Figure 7:
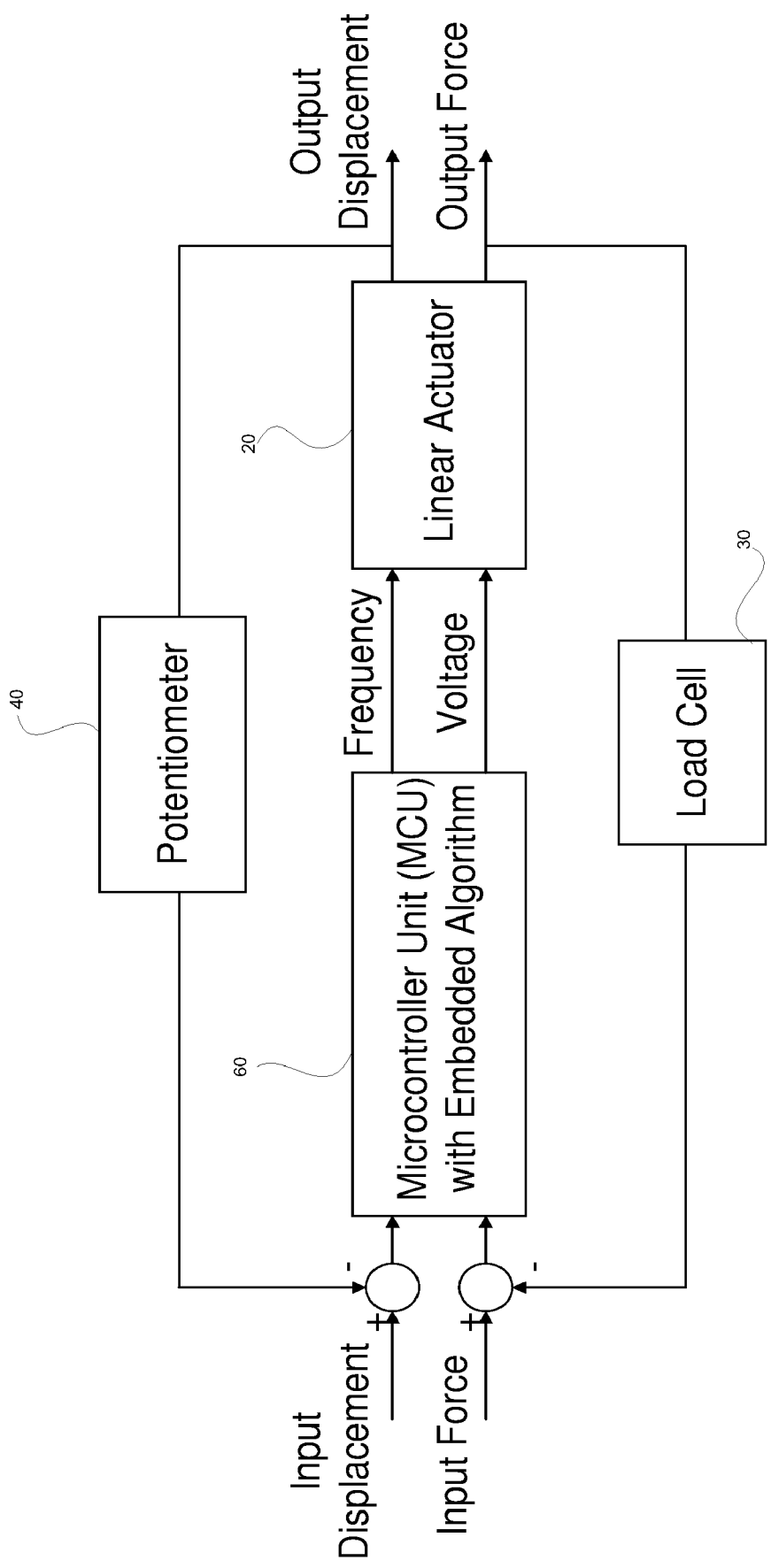
FIG. 7 is a block diagram of a wearable device in accordance with an embodiment of the present invention.

The linear actuator 20 is positioned on an inner side of the limbs as depicted in FIGS. 1 to 4 or on a lateral side of a limb as depicted in FIGS. 5 and 6. The positioning depends on which limb is to be assisted. For legs, positioning on their lateral side is preferred. For arms, positioning on the inner side is preferred. The device 10 may be worn the upper and lower limb joints, including the wrist, elbow, knee, and ankle.

Referring to FIGS. 5 and 6, the position of the device 10 relative to the limbs 50, 51 is illustrated. Turning to FIG. 5, the positioning of the device 10 should be such that the joint 52 of the limbs 50, 51 is aligned with the centre of the distance traveled by the lead screw 21 moving forwards and half the forward distance traveled by the lead screw 21 together with the length of the load cell 30, motor of the linear actuator 20 and the full travel distance traveled by the lead screw 21 moving backwards should equal the length of the upper limb 51. The dotted lines shows the position of the hinge 11 connected at a forward end of the lead screw 21 when the linear actuator 20 contracts/retracts. Turning to FIG. 6, the limbs 50, 51 are bent caused by the assistance provided by the device 10 and shows that the lead screw 21 has fully traveled backwards within the housing of the linear actuator 20. For example, if the stationary end of the linear actuator 20 is pivoted on the upper arm 19 cm away from the center of the joint 52, after deducting the distance of the (motor+load cell+hinge=4 cm), it is 15 cm. This distance is divided by three to be 5 cm, which is half of the travel distance of the lead screw 21. The total travel distance of the lead screw 21 is 5 cm multiplied by 2 which equates to 10 cm A pair of fastening members 12 is provided on the distal ends of the device 10 to secure the device 10 to the limbs 50, 51. As the lead screw 21 moves, the fastening members 12 also move with it causing the limbs 50, 51 to move in a bending or stretching motion by reducing the distance between the fastening members 12. Preferably, the fastening member is a stretchable or elastic strap/belt 12. The tightness around the limb 50, 51 may adjusted and set by releasing or engaging a Velcro portion or by using buttons. Part of the strap 12 is rigid and has hinges 11 to connect to the end of the linear actuator 20. The fastening members 12 may be exclusively interconnected by the linear actuator. The hinges 11 may be in the form of a pin or bolt passing through a hole in the device 10 and a rigid member of the strap 12. The strap 12 needs to be tight enough to prevent any sliding of the device 10 relative to the limb 50, 51 but not too tight which would become uncomfortable for the user.

Figure 8:
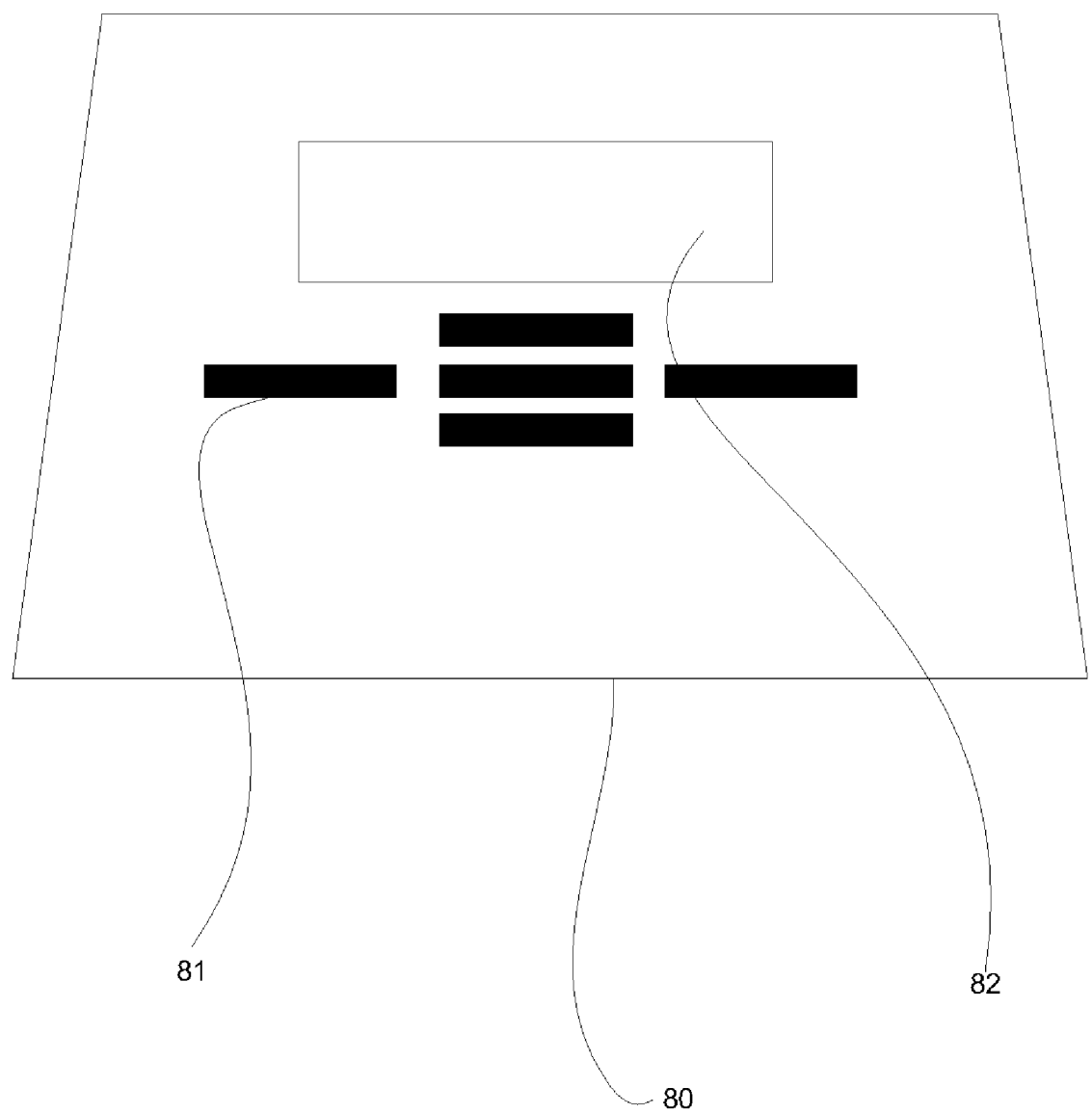
FIG. 8 is a pictorial diagram of a portable control unit in accordance with another embodiment of the present invention.
Figure 9:
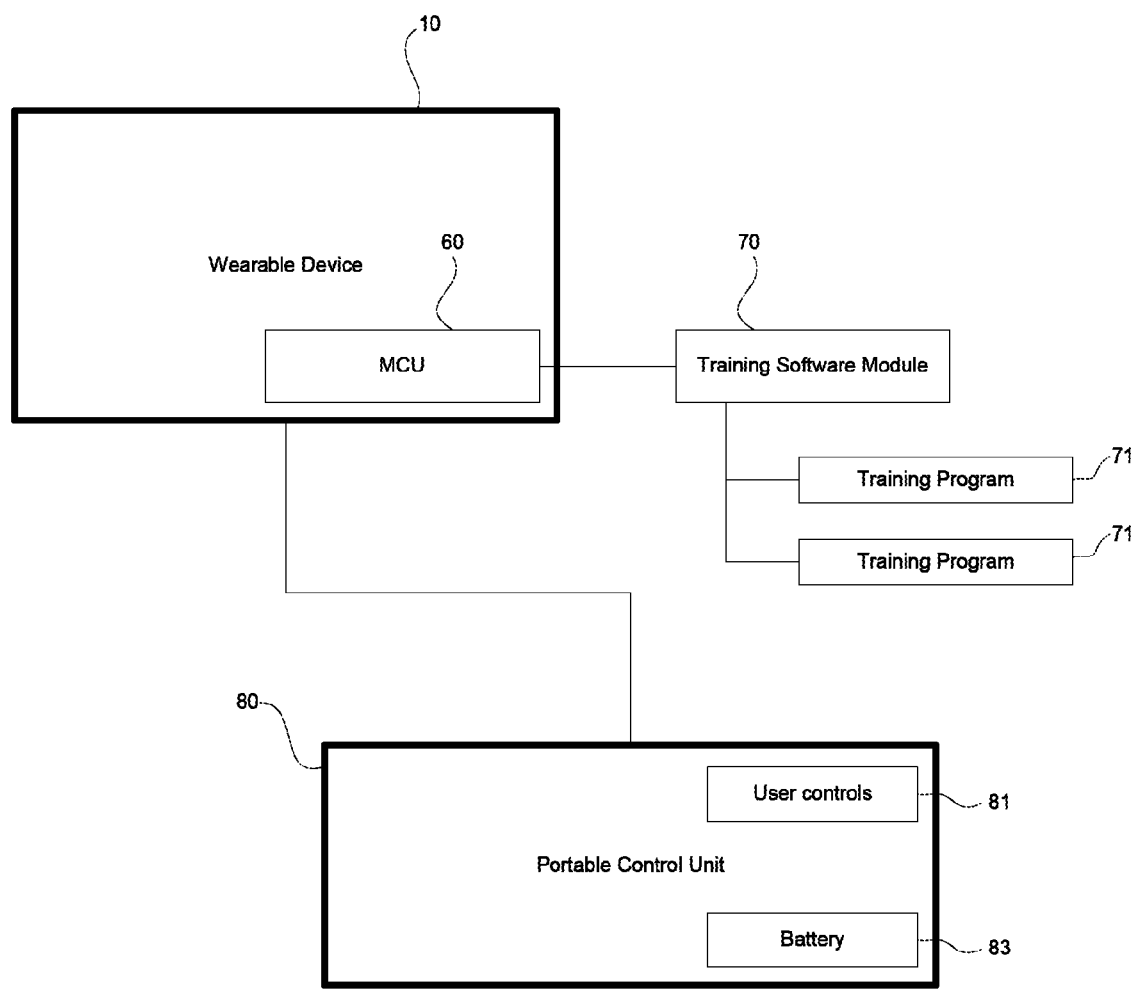
FIG. 9 is a system diagram of a system for controlling and operating a wearable device in accordance with another embodiment of the present invention.

Referring to FIGS. 8 and 9, a portable control. unit 80 operatively connected to the linear actuator 20 is provided. The control. unit 80 includes a battery 83 to supply power to the linear actuator 20 and other electrically powered units via electrical. cable. The control. unit 80 may be attached to the waist belt around the user to free the use of the user's arms. The control. unit 80 has an LED display 82 with five navigation buttons 81 for menu-driven control. The user may input the amount of force required, run a training program 71 or activate/deactivate the device 10, etc. The control. signals from the control. unit 80 to the device 10 may be transmitted wirelessly or via cable. The electronics of the control. unit 80 are miniaturized to fit on a printed circuit board (PCB) roughly the size of cellular phone.

In a typical scenario, the user intends to make a movement with their limbs 50, 51. The load cell 30 measures the force as the user is making the movement. If the force is greater than the stationary threshold, the linear actuator 20 actuates with a velocity proportional to the force measured by the load cell 20. Actuation of the linear actuator 20 continues until the load cell 20 measures a force that falls below the stationary threshold. For example, if the weight of a forearm is 2 kg, when the load cell 30 detects the force to be 1.9 kg (with a force change (2-1.9) kg=0.1 kg=100 g), which is more than the stationary threshold of 50 g, the linear actuator 20 will be triggered based on the detected force change 100 g to actuate by a proportional amount, for example, pulling back the lead screw 21 for 1 mm in 1 second with a velocity of 1 mm/sec. The load cell 30 will pick up the next force change as the intention of movement for the next step. If the force change remains the same or is increasing, it means the user would like to bend his/her arm more. If the force change is decreasing, the user may want to go backward to adjust to a proper position.

Although a linear actuator 20 with a lead screw 21 has been described, it is envisaged that other devices capable of generating linear motion may be used. For example, a linear motor or linear actuators without a rotating lead screw may be used.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. A wearable device to assist with the movement of limbs connected at a joint, the device comprising: a linear actuator having a motor that is capable of generating linear motion in a controlled and incremental manner by converting rotary motion, a first limb fastener for attaching to a first limb and a second limb fastener for attaching to a second limb, the limb fasteners being exclusively interconnected by the linear actuator's respective distal ends; the combination of the limb fasteners and the linear actuator configured such that linear motion generated by the linear actuator imparts an active force to move and pivot the limbs about the joint, wherein the active force exclusively augments voluntary limb movement; a load cell configured to measure a force applied to the linear actuator; a potentiometer configured to measure the displacement of the linear actuator when linear motion is generated; and a microcontroller unit for processing the force and displacement measurements, wherein when a measured change of force applied by the limbs to the linear actuator is greater than a pre-defined stationary threshold, the microcontroller unit activates the linear actuator to generate a linear motion correlated to the measured change of force above the stationary threshold and the displacement, thereby providing an assistive force.

2. The device according to claim 1, wherein the potentiometer is positioned on a lead screw of the linear actuator.

3. The device according to claim 1, wherein the microcontroller unit is further configured to process a feedback control loop to control the operation of the linear actuator using a feedback signal transmitted from the load cell or the potentiometer.

4. The device according to claim 3, wherein the displacement measured by the potentiometer and a time value is recorded.

5. The device according to claim 4, further comprising a training software module to evaluate the performance of a user using the wearable device in a training exercise by comparing the difference between the recorded displacement and time value against a reference displacement and time value.

6. The device according to claim 1, wherein the amount of force and displacement of the linear motion generated by the linear actuator is adjustable depending on whether a user is considered beginner, intermediate or advanced in the level of assistance they require.

7. The device according to claim 1, wherein the device is configured to be positioned on an inner side of the limbs or on a lateral side of a limb.

8. The device according to claim 1, further comprising a portable control unit operatively connected to the linear actuator, the portable control unit including a battery to supply power to the linear actuator.

9. A method for assisting with the movement of limbs connected at a joint, the method comprising: providing a configuration that includes a linear actuator and two limb fasteners, the linear actuator exclusively interconnecting the two limb fasteners, and the linear actuator having a motor capable of generating linear motion in a controlled and incremental manner by converting rotary motion; attaching the configuration to the limbs connected at the joint, using the limb fasteners, such that linear motion generated by the linear actuator imparts an active force to move and pivot the limb about the joint, wherein said active force exclusively augments voluntary limb movement; measuring a change of force applied to the linear actuator; measuring the displacement of the linear actuator when linear motion is generated; and generating linear motion having a predetermined velocity using the linear actuator to assist with the movement of the limbs based on when the measured change of force applied by the limbs to the linear actuator is greater than a pre-defined stationary threshold, and wherein the linear motion generated is correlated with the extent to which the measured change of force exceeds the stationary threshold and the displacement.

10. A system for assisting with the movement of limbs connected at a joint, the system comprising: a linear actuator having a motor capable of generating linear motion in a controlled and incremental manner by converting rotary motion; a first limb fastener for attaching to a first limb and a second limb fastener for attaching to a second limb, the limb fasteners being exclusively interconnected by the linear actuator's respective distal ends; the combination of the limb fasteners and the linear actuator configured such that linear motion generated by the linear actuator imparts an active force to move and pivot the limb about the joint, wherein said active force exclusively augments voluntary limb movement; a load cell configured to measure a force applied to the linear actuator; a potentiometer configured to measure the displacement of the linear actuator when linear motion is generated; a portable control unit operatively connected to the linear actuator, the portable control unit comprising a battery to supply power to the linear actuator and a processor configured to control the level of assistance generated by the linear actuator; and a microcontroller unit for processing the force and displacement measurements, wherein when a measured change of force applied by the limbs to the linear actuator is greater than a pre-defined stationary threshold, the microcontroller unit activates the linear actuator to generate a linear motion correlated to the measured change of force above the stationary threshold and the displacement, thereby providing an assistive force.

* * * * *